(12) United States Patent
Sakurada

(10) Patent No.: US 7,537,342 B2
(45) Date of Patent: May 26, 2009

(54) SUBJECTIVE OPTOMETRIC APPARATUS

(75) Inventor: Tomohiro Sakurada, Tokyo (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 143 days.

(21) Appl. No.: 11/784,653

(22) Filed: Apr. 9, 2007

(65) Prior Publication Data
US 2007/0236665 A1 Oct. 11, 2007

(30) Foreign Application Priority Data
Apr. 11, 2006 (JP) ............................. 2006-108335

(51) Int. Cl.
*A61B 3/02* (2006.01)
(52) U.S. Cl. ..................................................... 351/222
(58) Field of Classification Search ................. 351/211, 351/222, 227, 241, 243, 245, 246, 200, 205, 351/237, 238, 239; 359/624, 710
See application file for complete search history.

(56) References Cited

U.S. PATENT DOCUMENTS 5,929,972 A * 7/1999 Hutchinson .................. 351/237
7,407,289 B2 * 8/2008 Sakurada ..................... 351/211

2004/0141152 A1 7/2004 Marino et al.

FOREIGN PATENT DOCUMENTS

| DE | 196 15 949 A1 | 10/1996 |
|---|---|---|
| JP | 2002-143092 | 5/2002 |
| WO | WO 02/076301 A1 | 10/2002 |

* cited by examiner

*Primary Examiner*—Ricky L Mack
*Assistant Examiner*—Tuyen Q Tra
(74) *Attorney, Agent, or Firm*—Chapman and Cutler LLP

(57) ABSTRACT

A subjective optometric apparatus includes: a target-presenting device; an optical element-arranging device configured to set optical elements between the target-presenting device and eyes to be examined; and a controller configured to control the target-presenting device and the optical element-arranging device. The controller includes: a memory configured to store at least detailed contents of examinations and target charts; a display configured to display an operation screen including at least a target chart field corresponding to the target chart currently displayed on the target-presenting device and a target chart selection button screen field having a plurality of changeover screen fields in which target chart selection buttons for selecting the corresponding target charts to be presented are arranged and displayed; a registration section configured to associate the detailed contents and the target chart selection buttons and register the associated target chart selection buttons; and a control section configured to control the target-presenting device according to the target chart selection buttons, and control the optical element-arranging device such that the optical element corresponding to the detailed contents associated with the specified target chart selection button is set.

10 Claims, 7 Drawing Sheets

SUBJECTIVE OPTOMETRIC APPARATUS

PRIORITY CLAIM

The present application is based on and claims priority from Japanese Application Number 2006-108335, filed Apr. 11, 2006, the disclosure of which is hereby incorporated by reference herein in its entirety.

BACKGROUND

The present invention relates to a subjective optometric apparatus. More particularly, the invention relates to a subjective optometric apparatus in which optometry is conducted by presenting target charts for examining visual performance to an examinee and an examiner asks questions to the examinee related to how the presented target charts are perceived by the examinee.

Conventionally, there has been known a subjective optometric apparatus, such as the apparatus disclosed in Japanese patent publication No. 2002-143092 for example. JP2002-143092A discloses a subjective optometric apparatus including a target-presenting device, an optical element-arranging device, and a controller, and in which examination of the eyes of the examinee to be examined is performed according to examination programs. The target-presenting device shows charts including targets for examining the visual performance of the eyes to be examined, the optical element-arranging device arranges various optical elements for optically correcting the visual performance of the eyes to be examined between the target-presenting device and the eyes, and the controller controls the target-presenting device and the optical element-arranging device.

According to the disclosure of JP2002-143092A, the controller is generally structured of a manipulating section, a display, a mouse device and a memory. The manipulating section or the mouse is manipulated to select the target chart to be displayed on the target-presenting device and to control the optical elements to be arranged in the optical element-arranging device.

The display is structured of a liquid crystal display panel. The manipulating section is provided with selection switches or selection buttons for selecting the target chart to be displayed. The memory includes an external storage device such as a hard disk, in which the target charts corresponding to the selection switches are stored.

In the conventional subjective optometric apparatus, addition, alteration and deletion of the target charts to be displayed to the examinee can be easily done by utilizing software.

However, according to the conventional subjective optometric apparatus including JP2002-143092A, the selection switches for selecting the target charts are structured based on hardware. Accordingly, when target charts to be displayed to the examinee are to be added, selection switches for selecting the added target charts have to be added in a hardware-based manner. Hence, the number of selection switches increases in accordance with an increase in the target charts to be displayed to the examinee, which makes it difficult for the examiner to figure out on which part of the manipulating section the selection switch corresponding to the target chart to be displayed is disposed. Therefore, there has been a problem in the conventional subjective optometric apparatus including JP2002-143092A in that a prompt optometry process is disturbed. This problem also applies to a case in which a list of the selection switches or the target chart selection buttons is displayed on the liquid crystal display panel in a software-based manner.

SUMMARY

At least one objective of the present invention is to provide a subjective optometric apparatus capable of enhancing the convenience of manipulation by an examiner and of enhancing the convenience of examination of the eyes of an examinee even when the number of target charts to be displayed on a target-presenting device is increased.

To achieve these and other advantages and in accordance with the purpose of the invention, as embodied and broadly described herein, the invention provides a subjective optometric apparatus, which includes: a target-presenting device configured to display target charts for examining visual performance of eyes to be examined; an optical element-arranging device configured to set optical elements for optically correcting the visual performance of the eyes to be examined between the target-presenting device and the eyes to be examined; and a controller configured to control the target-presenting device and the optical element-arranging device, the controller including: a memory configured to store at least detailed contents of examinations to be performed on the eyes to be examined and the target charts; a display configured to display an operation screen including at least a target chart field corresponding to one of the target charts currently displayed on the target-presenting device and a target chart selection button screen field, the target chart selection button screen field having a plurality of changeover screen fields in which target chart selection buttons for selecting the corresponding target charts to be presented according to the examinations to be performed are arranged and displayed; a registration section configured to associate the detailed contents of the examinations and the target chart selection buttons and configured to register the associated target chart selection buttons; and a control section configured to control the target-presenting device to display one of the target charts selected by specification of a corresponding one of the target chart selection buttons of the target chart selection button screen field, and configured to control the optical element-arranging device such that one of the optical elements corresponding to the detailed contents associated with the specified one of the target chart selection buttons is set between the eyes to be examined and the target-presenting device.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DETAILED DESCRIPTION

Figure 1:
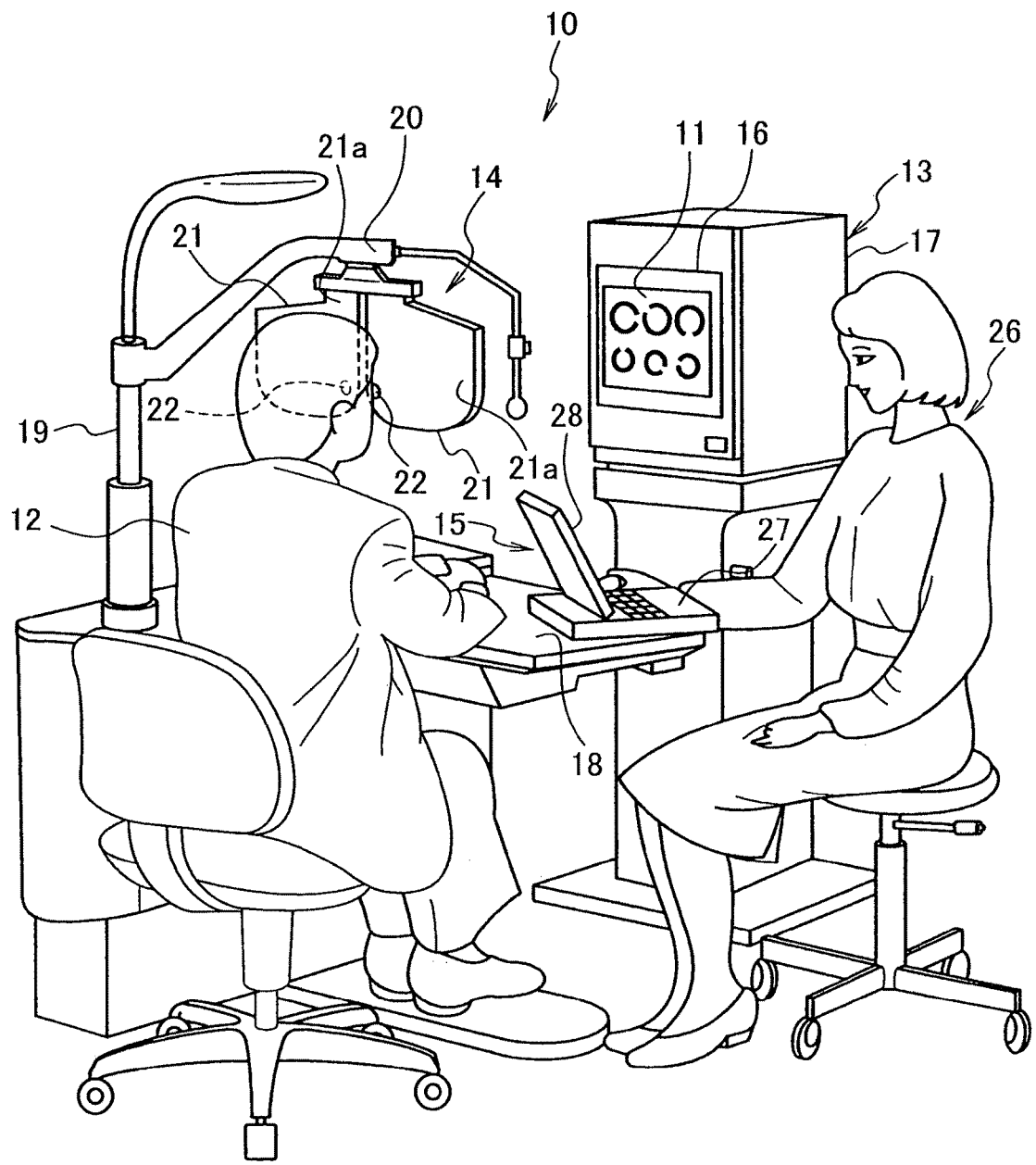
FIG. 1 is a perspective view schematically illustrating a subjective optometric apparatus according to an embodiment of the present invention.

Reference will now be made in detail to the present preferred embodiments of the invention, examples of which are illustrated in the accompanying drawings. Wherever possible, the same reference numbers are used in the drawings and the description to refer to the same or like parts. The scope of the present invention, however, is not limited to these embodiments. Within the scope of the present invention, any structure and material described below can be appropriately modified.

Referring to FIG. 1, reference numeral 10 denotes a subjective optometric apparatus, reference numeral 12 denotes an examinee, reference numeral 18 denotes an optometry table, and reference numeral 26 denotes an examiner.

As illustrated in FIG. 1, the subjective optometric apparatus 10 is provided with a target-presenting device 13 for displaying various target charts 11 to of the examinee 12 the eyes to be examined, and a correction device 14 for correcting visual performance of the eyes to be examined. In the present embodiment, the subjective optometric apparatus 10 is used to determine dioptric power of lenses of unillustrated spectacles when spectacles are to be made for example.

The target-presenting device 13 includes a presenting device body 17. The presenting device body 17 is provided with a display window 16 on which the target chart 11 is displayed. The target chart 11 displayed on the display window 16 is selected by operation of a controller 15 or a controlling device 15 having functions described later.

The optometry table 18 is provided with a support pillar 19 which extends from the optometry table 18 upwards. An upper part of the support pillar 19 is provided with an arm 20 extending in a lateral direction. The correction device 14 is attached to the arm 20.

The correction device 14 includes a pair of phoropters 21 disposed horizontally in a juxtaposed manner. Each of the phoropters 21 includes a housing 21a and an optometry window 22.

Inside of each housing 21a is rotatably disposed a well-known ring-like lens disk which is unillustrated. In the lens disk, lenses for example as a plurality of well-known optical elements having mutually-different refractivities are provided along a circumferential direction of the lens disk.

The correction device 14 constitutes an optical element-arranging device which selectively arranges the optical elements between the eyes of the examinee 12 to be examined and the target-presenting device 13. Each of the lenses and so on is selectively disposed in each of the corresponding optometry windows 22 by rotation of the lens disk by the controller 15.

Figure 2:
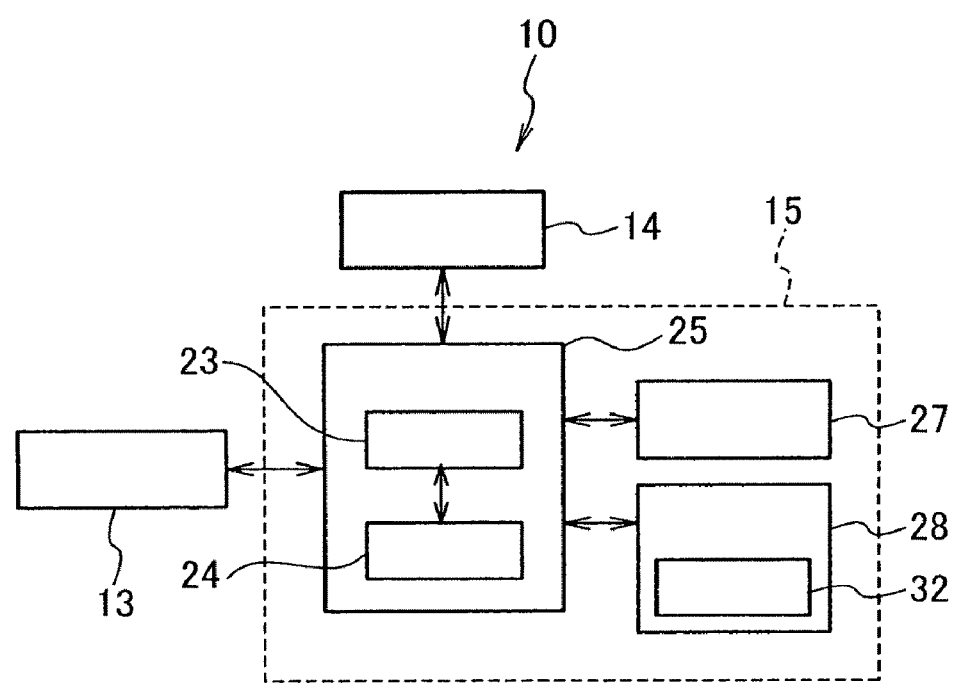
FIG. 2 is a block diagram schematically illustrating the subjective optometric apparatus according to the embodiment of the present invention.
Figure 3:
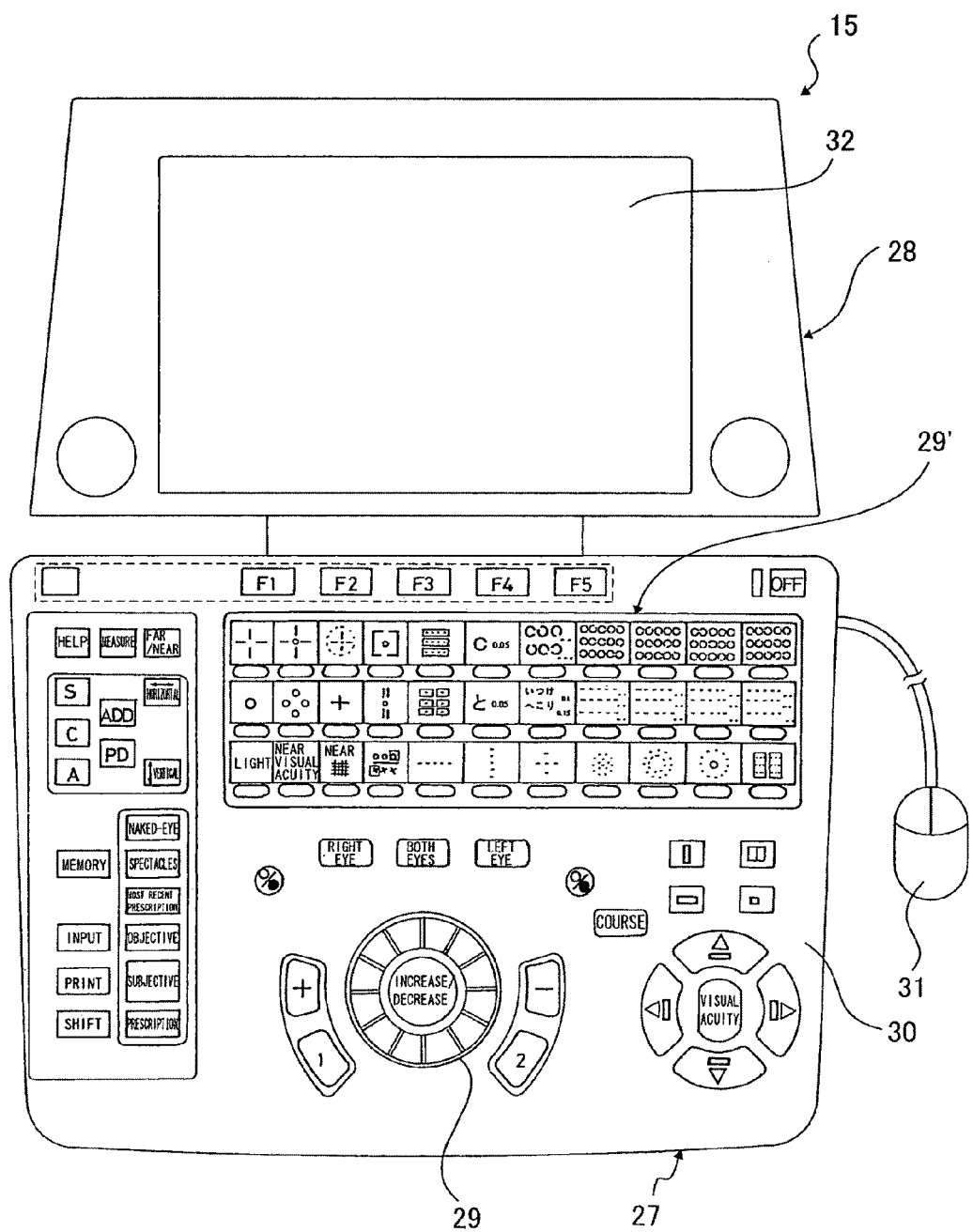
FIG. 3 is a plan view schematically illustrating a controller according to the embodiment of the present invention.

Referring to FIGS. 2 and 3, the controller 15 includes an arithmetic control circuit 25, a manipulating section 27, and a display 28 electrically connected with the manipulating section 27. The arithmetic control circuit 25 has a CPU (Central Processing Unit) 23 or a control section 23 and a memory 24. The display 28 is structured of a liquid crystal display panel in the present embodiment, although it is not limited thereto.

The manipulating section 27 and the display 28 are each connected to the arithmetic control circuit 25. The CPU 23 is connected with an unillustrated drive control section provided in each of the correction device 14 and the target-presenting device 13.

The memory 24 stores therein, for example, various examination data such as naked-eye data including, for example, spherical diopter power, astigmatism degree and an axis angle of the eyes to be examined at the time when the eyes are naked, and spectacle data including, for example, spherical diopter power, astigmatism degree and an axis angle of the spectacles currently being used. Also, the various target charts 11, programs for executing plural kinds of examinations such as a spherical degree test, astigmatism test and a test for infants, and detailed contents or parameters for the examinations and so forth are stored for example. The CPU 23 controls arrangement of the respective lenses in each of the optometry windows 22 according to contents of examination data read from the memory 24.

When an unillustrated power of the manipulating section 27 is turned on for example, an unillustrated menu screen is displayed on the display 28. An operation screen 32 which will be described later in detail is displayed when a corresponding item of the operation screen 32 is selected from items displayed on the menu screen.

In the present embodiment, the manipulating section 27 is structured of a control panel 30 and a mouse device 31. The control panel 30 for example includes a dial switch 29, target chart selection buttons 29' and so on.

Figure 4:
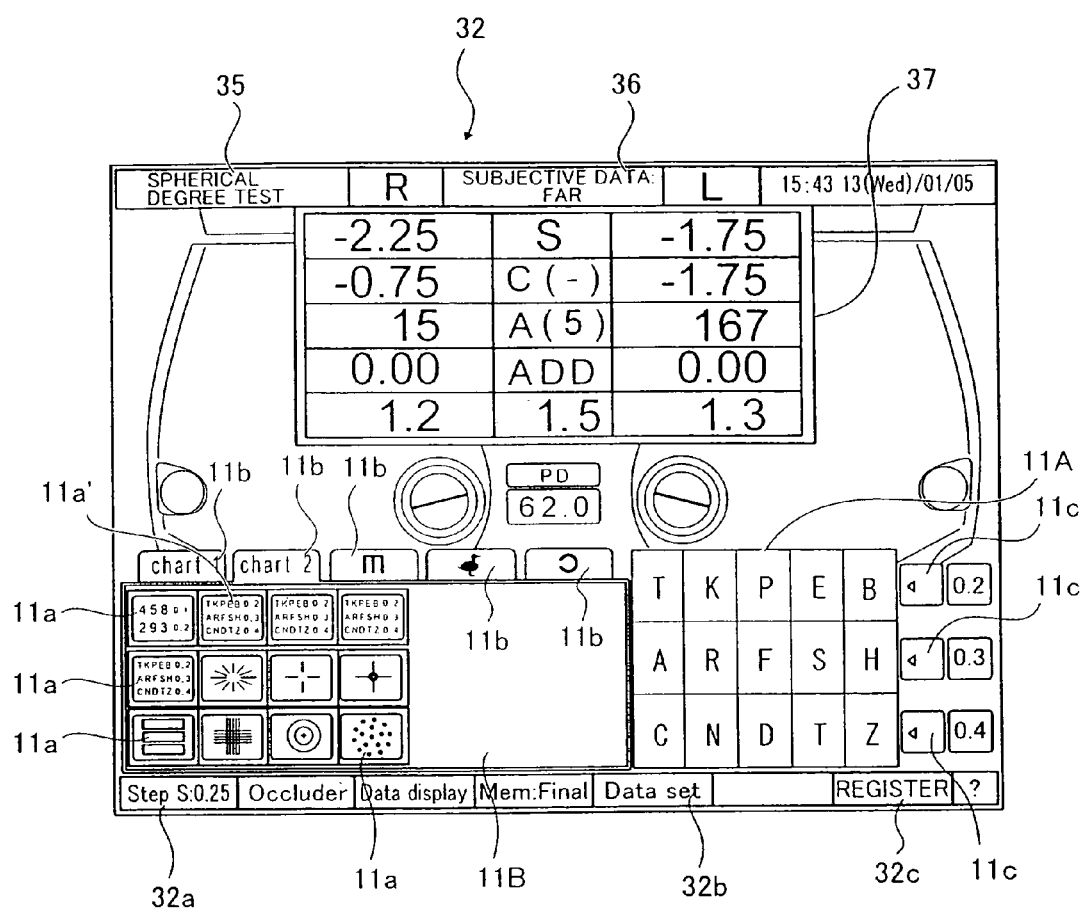
FIG. 4 schematically illustrates an operation screen of a display according to the embodiment of the present invention.

The dial switch 29 is used for example to change numerical values of the spherical diopter power, the astigmatism degree and the axis angle displayed on a data display field 37 of the operation screen 32 illustrated in FIG. 4. When the dial switch 29 of the control panel 30 is manipulated, a control signal is sent from the CPU 23 to the unillustrated drive control section of the correction device 14. Thereby, for example, the lens having the refractivity set by the manipulation of the dial switch 29 is arranged in the optometry window 22 of each of the phoropters 21.

The operation screen 32 includes a target chart field 11A which corresponds to the target chart 11 being displayed on the target-presenting device 13, and a target chart selection button screen field 11B in which target chart selection buttons 11a for selecting the target charts 11 to be presented according to the examinations to be performed are arranged and displayed. Each of the target chart selection buttons 11a is preferably displayed in the target chart selection button screen field 11B as a thumbnail image.

A lower part of the operation screen 32 is provided with various operation buttons which are, for example but not limited thereto, a stepwise button 32a for increasing and decreasing diopter of the lens in 0.25 diopter increments in a stepwise manner, a data set button 32b for setting data on subjective data, objective data, prescription data, most recent prescription data, naked-eye data and so on, and a registration button 32c for displaying a later-described registration screen 33 on the display 28.

An upper part of the operation screen 32 includes, for example, an item 35 indicating the name of the examination currently being performed, an item 36 indicating the name of detailed contents of the examination, and items corresponding to data on the right eye and data on the left eye of the data display field 37.

According to the present embodiment of the invention, the target chart selection button screen field 11B includes a plurality of changeover screens. An upper part of the target chart selection button screen field 11B is provided with changeover buttons 11b or tabs 11b corresponding to the respective changeover screens. Each of the changeover buttons 11b has meaning information attached for providing meaning to the changeover screen.

In the present embodiment, meanings of "chart 1", "chart 2", a symbol "E" and a duck-shaped figure are given for the changeover buttons 11b, respectively. FIG. 4 illustrates by way of example a case in which the changeover button 11b of the "chart 2" is selected, and the twelve target chart selection buttons 11a, which are ordered and registered by setting of the examiner, are categorized by the examinations to be performed and displayed in the target chart selection button screen field 11B.

In addition, FIG. 4 illustrates by way of example the case in which the plurality of target charts corresponding to visual acuity of "0.1 to 0.4" is arranged and displayed on the target chart selection button screen field 11B. Furthermore, the meaning that the "chart 2" is used for subjective examination of a nearsighted person having visual acuity of 0.5 or less is given to the "chart 2", whereas the meaning that the "chart 1" is used for objective examination is given to the "chart 1". To the "duck-shaped figure", the meaning that the "duck-shaped figure" is used for examination of the infant is given.

It is to be noted that aggregations of target chart selection buttons 11a used for the remaining examinations are hidden behind a window of the target chart selection button screen field 11B. A page of the changeover screen is turned when the examiner operates the desired changeover button 11b, and thereby, the aggregation of target chart selection buttons 11a in which the target chart selection buttons 11a corresponding to the changeover screen selected with the desired changeover button 11b by the examiner are aligned, is displayed in the target chart selection button screen field 11B.

In the operation screen 32 illustrated in FIG. 4, a target chart selection button of the target chart selection buttons 11a denoted as 11a' is selected and displayed in the target chart field 11A. FIG. 4 illustrates an example in which the target charts 11 presented on the target-presenting device 13, numbers representing visual acuity values of the examinee, and mask buttons 11c are displayed in the target chart field 11A.

Note that there are four identical target chart selection buttons 11a including "TKP . . . TZ" arranged and displayed in the same changeover screen in the target chart selection button screen field 11B. However, these target chart selection buttons 11a are each associated with examination contents having mutually different contents, which will be described later in detail.

According to the present embodiment, registration of the target chart selection button(s) 11a in the target chart selection button screen field 11B is carried out by specifying a registration button 32c with the mouse 31.

Figure 5:
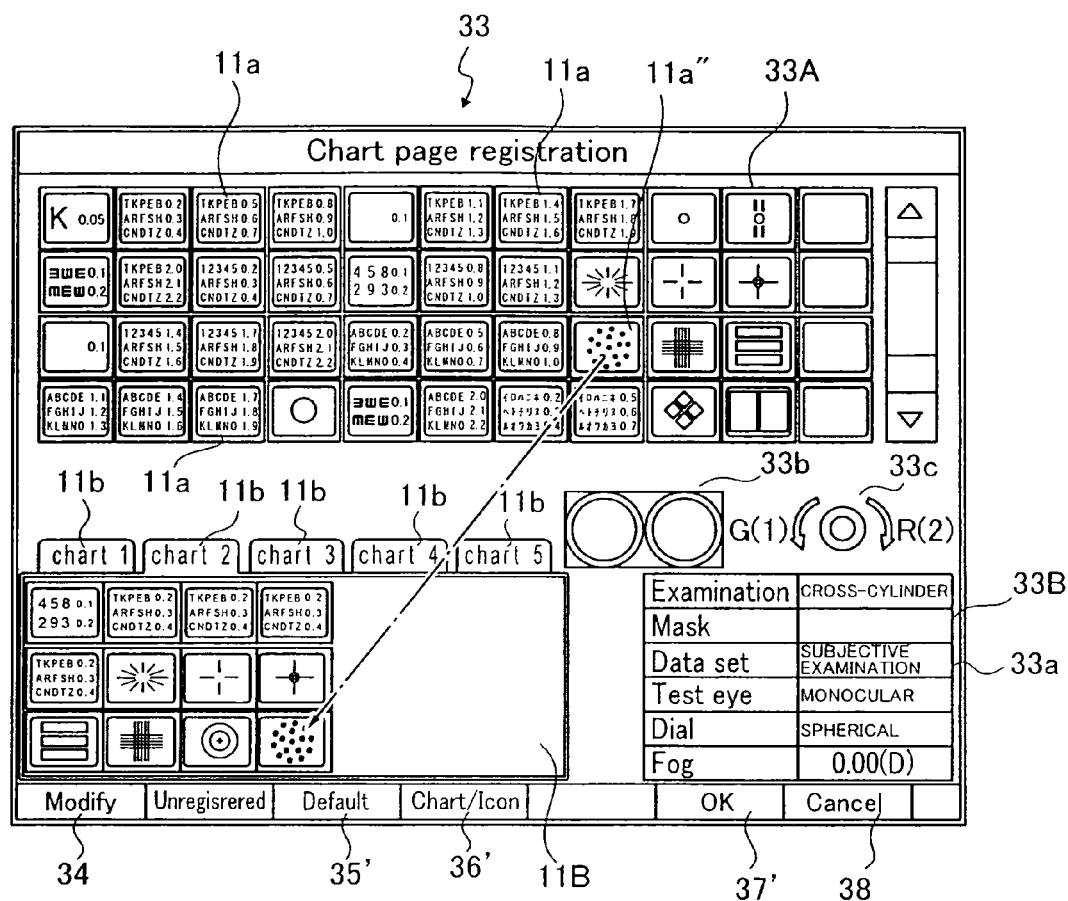
FIG. 5 schematically illustrates a registration screen of the display according to the embodiment of the present invention.

When the mouse 31 is manipulated to place an unillustrated cursor on the registration button 32c and the registration button 32c is pressed by a click of the mouse 32, displaying of the display 28 changes from the operation screen 32 to the registration screen 33 illustrated in FIG. 5. The registration screen 33 together with the mouse 31 constitute a registration section.

The registration screen 33 includes a list screen field 33A having a list of various target chart selection buttons 11a, the target chart selection button screen field 11B, and a detailed content display field 33B which displays detailed contents associated with each of the target chart selection buttons 11a in the list screen field 33A.

FIG. 5 illustrates by way of example a case in which the changeover button 11b of the "chart 2" is specified for the changeover screen, the eleven target chart selection buttons 11a are already registered in the changeover screen of the "chart 2", and a target chart selection button denoted as 11a" is to be newly registered in the "chart 2".

In the present embodiment, the mouse 31, preferably in cooperation with the registration button 32c, plays a role as a specifier which associates each of the target chart selection buttons 11a displayed in the list screen field 33A of the registration screen 33 with the target chart selection button screen field 11B. The mouse 31 is manipulated to locate the unillustrated cursor on the target chart selection button 11a", and the target chart selection button 11a" is then moved to the changeover screen of the "chart 2", for example by means of a drag-and-drop operation, to register the target chart selection button 11a" in the "chart 2".

The detailed content display field 33B displays the detailed contents associated with the target chart selection button 11a", in accordance with the registration of the target chart selection button 11a" in the changeover screen of the "chart 2".

For example, the detailed content display field 33B displays an item 33a indicating that a cross-cylinder is used for the examination, data for the subjective examination is set for the "Data set", only one eye is subjected to the examination, the dial is set to spherical, and an amount of fogging is zero diopter. The detailed content display field 33B also displays a FIG. 33b indicating that the lens utilized for the examination is unused, and a FIG. 33c indicating a red-green test. The item 33a, the FIG. 33b and the FIG. 33c illustrated in FIG. 5 are displayed in the detailed content display field 33B as a default or initial setting.

A lower part of the registration screen 33 includes a modify button 34 for changing the association between the target chart selection button 11a and its corresponding detailed contents of the examination, a default button 35' for setting default values to displayed contents in the detailed content display field 33B of the registration screen 33, a Chart/Icon setting button 36', a determine button 37', and a cancel button 38.

The Chart/Icon setting button 36' is for changing the meaning information attached to the changeover buttons 11b. When the Chart/Icon setting button 36' is operated, the displaying on the display 28 changes from the registration screen 33 to a meaning information modification screen 100. The meaning information modification screen 100 includes a list screen 110 for displaying a list of various icons, characters and so on, and the target chart selection button screen field 11B illustrated in FIG. 5 for example.

For example, the changeover button 11b attached with the "chart 4" is replaced with an icon representing the duck-shaped figure, when, by the manipulation of the mouse 31, the unillustrated cursor is placed on the icon representing the duck-shaped figure in the list screen 110 and then the icon representing the duck-shaped figure is moved to a position attached with the "chart 4" of the changeover button 11b by means of the drag-and-drop operation for example to register.

Figure 6:
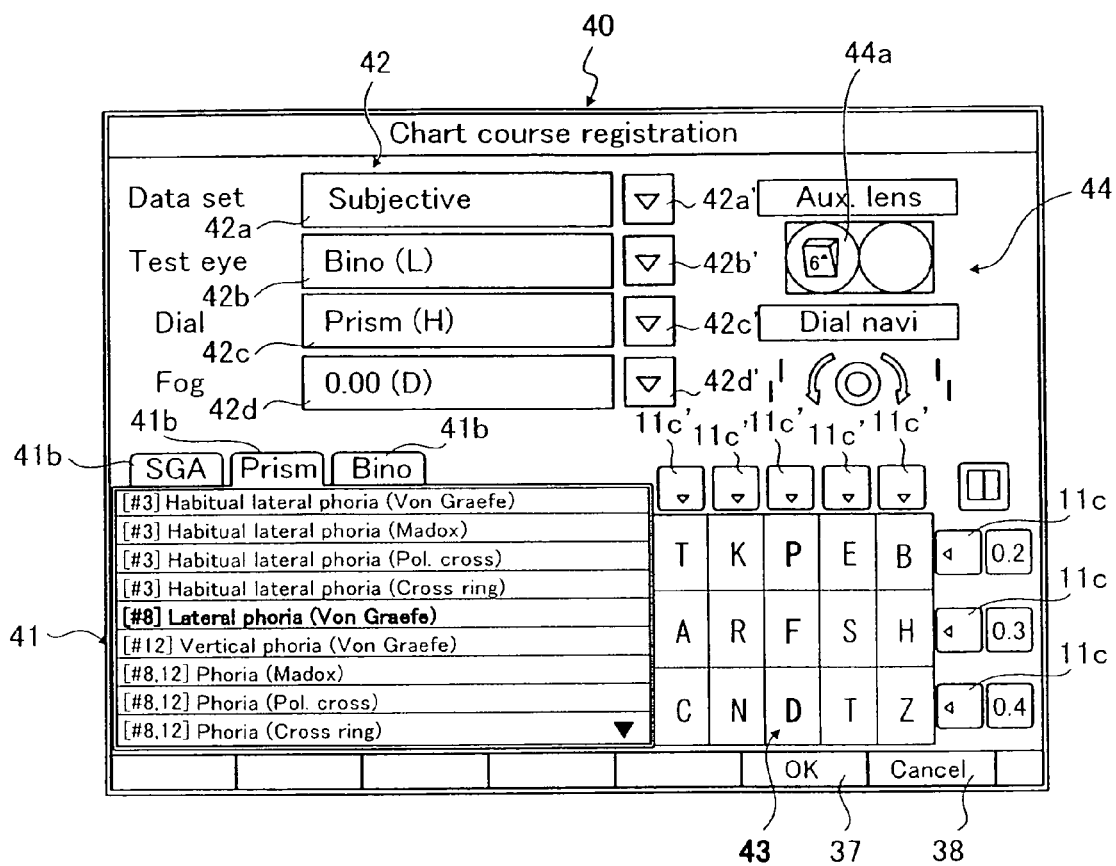
FIG. 6 schematically illustrates a modification setting screen of the display according to the embodiment of the present invention.
Figure 7:
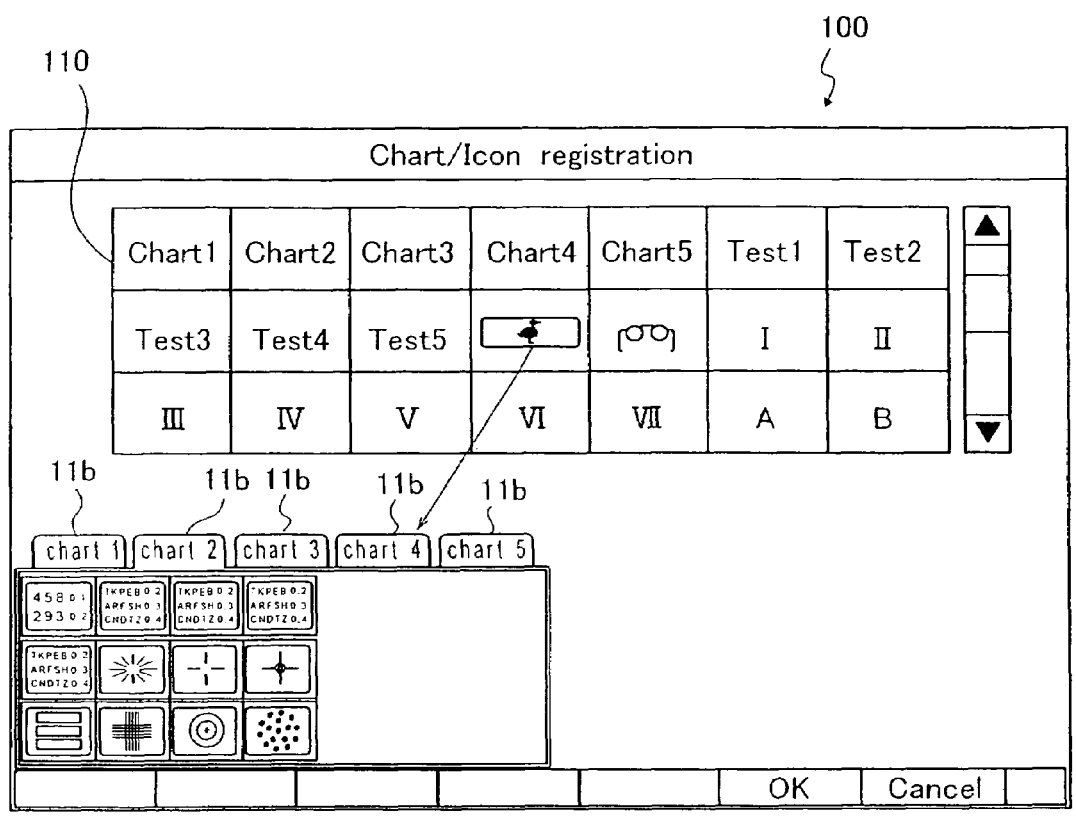
FIG. 7 schematically illustrates a meaning information modification screen of the display according to the embodiment of the present invention.

Referring to FIG. 5, the displaying of the display 28 changes from the registration screen 33 to a modification setting screen 40 illustrated in FIG. 6, when the modify button 34 is operated in the registration screen 33 with the mouse 31. The modification setting screen 40 for example includes a display field 41 for displaying the kinds of examination, a display field 42 for displaying the parameters representing the detailed contents of the examination desired to be performed, a target chart field 43 for displaying the target charts registered immediately before in the registration screen 33, and a display field 44 for displaying an optical element used in the examination to be performed. FIG. 6 illustrates by way of example a case in which a FIG. 44a representing an auxiliary lens (represented as Aux. lens in FIG. 6) is displayed in the display field 44. The auxiliary lens here is a prism, and characters representing dioptric power of the prism are displayed in the FIG. 44a.

In the present embodiment, the kinds of examination include examination on the spherical diopter power, the astigmatism degree and the axis angle, examination on prisms, and examination on both eyes and so forth, although they are not limited thereto. An upper part of the display field 41 includes changeover buttons 41b or tabs 41b for changing over one screen of the display field 41 to another screen of the display field 41.

FIG. 6 illustrates by way of example a case in which the examination on the prisms is selected, various tests on the examination on the prisms are displayed in the display field 41, and a lateral phoria examination is selected among the various tests on the examination on the prisms. In addition, the target chart selection button 11a' illustrated in FIG. 4 is selected for the target chart selection button used for the lateral phoria examination.

It is possible for the examiner to apply masking to the target chart 11 by using the mask button 11c or a mask button 11c'. The mask button 11c is used to apply the masking in a horizontal direction of the target chart 11, whereas the mask button 11c' is used to apply the masking in a vertical direction of the target chart 11.

Referring to FIG. 6, the display field 42 includes a data set item 42a for setting data on the subjective examination, the objective examination, the spectacles, the prescription, the most recent prescription, or the naked-eye for example. The display field 42 also includes a test eye item 42b representing whether the examination is a monocular test for the left eye, a monocular test for the right eye or a binocular test, and a dial item 42c for setting an auxiliary lens such as open or without the auxiliary lens, closed or with a shielding plate, a pin-hole plate, a polarization plate, a prism and so on. Furthermore, the display field 42 includes a fogging amount item 42d for determining the degree of fogging, and pull-down buttons 42a' to 42d' are provided adjacent to the corresponding items, respectively.

The detailed contents according to a factory default or an initial setting are displayed in the modification setting screen 40 when the examiner has not changed any association between the target chart selection button 11a and its detailed contents.

It is possible for the examiner to freely modify the contents according to the factory default by manipulating the mouse 31. For example, the unillustrated cursor is located on the pull-down button 42a' by the use of the mouse 31 to display a pull-down screen including, for example, the data on the subjective examination, the objective examination, the spectacles, the prescription, the most recent prescription, and the naked-eye on the modification setting screen 40. Then, when the data on the subjective examination is selected among the items of the pull-down screen in a case in which the data on the naked-eye is set as the initial setting, the data on the naked-eye is changed to the data on the subjective examination.

In addition, when the monocular test for the left eye as the initial setting is set for the test eye item 42b, the examiner operates the pull-down button 42b' corresponding to the test eye item 42b by the use of the mouse 31 to display the pull-down screen on the modification setting screen 40. Thereby, it is possible for the examiner to set the test eye item 42b to the monocular test for the right eye or the binocular test. Hence, the contents of the target chart selection button 11a' are modified from the monocular test for the left eye to the monocular test for the right eye or the binocular test for example to be associated with the target chart selection button 11a' and registered.

Also, when a horizontal prism as the initial setting is set for the dial item 42c and a vertical prism is to be set for the dial item 42c for example, the pull-down button 42c' is operated by the use of the mouse 31 to display the pull-down screen on the modification setting screen 40 so as to select an item of the vertical prism. Thereby, it is possible for the examiner to set the vertical prism for the dial item 42c from the horizontal prism as the initial setting. Hence, the contents of the target selection button 11a' are modified from the horizontal prism to the vertical prism for example to be associated with the target chart selection button 11a' and registered.

Likewise, when an amount of fogging of zero diopter as the initial setting is set for a value of the fogging amount item 42d, it is possible for the examiner to set a desired value of fogging for the fogging amount item 42d by operating the corresponding pull-down button 42d'.

Therefore, by doing so, it is possible for the examiner to associate the target chart selection buttons with the various examinations and their detailed contents and to register the associated target chart selection buttons.

For example, when one of the plurality of target chart selection buttons which are identical to each other, such as the target chart selection button 11a' and the target chart selection button 11a" identical thereto, is to be registered by associating another kind of examination and the detailed contents therewith, the identical target chart selection button 11a" for example is selected in the registration screen 33. Then, the selected target chart selection button 11a" is registered in the changeover screen "chart 2" of the registration screen 33 for example by the drag-and-drop operation. Thereafter, the modify button 34 is operated by the manipulation of the mouse 31 to change over the screen of the display 28 from the registration screen 33 to the modification setting screen 40, in which an operation similar to that described in the foregoing is carried out.

Thereby, the target chart selection buttons at least identical to each other, for example the above-described target chart selection button 11a" identical to the target chart selection button 11a', which are associated with the contents of the examination different from each other are arranged and displayed in the same changeover screen "chart 2" of the target chart selection button screen field 11B.

Also, the target chart selection button 11a" identical to the target chart selection button 11a' can be registered in a changeover screen different from the changeover screen "chart 2" for example of the target chart selection button screen field 11B, by changing the changeover screens of the target chart selection button screen field 11B and registering the target chart selection button 11a" for example in the changed changeover screen. By doing so, it is possible to associate the target chart selection button 11a" with the contents of the examination different from those of the identical target chart selection button 11a'.

As described in the foregoing, when the arbitrary target chart selection button 11a is specified from the target chart selection buttons 11a registered in the target chart selection button screen field 11B, the corresponding contents of an examination associated with the specified target chart selection button 11a are displayed, in accordance with the present embodiment of the invention. The CPU 23 then controls the target-presenting device 13 and the correction device 14 such that the target chart corresponding to the target chart selection button 11a specified by the examiner is presented on the target-presenting device 13 and the optical element corresponding to the contents of the examination associated thereto is set in the correction device 14.

The subsequent optometric examinations are carried out by utilizing the operation screen 32, or by the manipulation of the manipulating section 27 for example.

Therefore, according to the present embodiment of the invention, the target charts selection buttons are configured to be selected, organized and registered by the examiner. Therefore, it is possible to create target chart selection buttons which are easy for the examiner to use. In addition, it is possible to associate the identical target chart selection buttons with the plurality of mutually different examinations, which correspond to the same target chart. Hence, it is possible to perform the plurality of examinations by the use of the same target chart, simultaneously.

Also, when a programmed examination is carried out in accordance with an order of alignment of the target chart selection buttons, it is convenient in that a flow of the examination can be visually understood.

Moreover, according to the embodiment of the invention, it is possible, if need arises, for the examiner to carry out an examination which is not incorporated in the programmed examination by opening the changeover screen while the programmed examination is performed. Therefore, it is possible to perform flexible examinations.

Note that, according to the present embodiment of the invention described above, the registration screen 33 together with the mouse 31 constitute the registration section. In one embodiment, a registration button is provided on the manipulating section 27, and the registration button provided on the manipulating section 27 is manipulated to select and register the target chart selection button. Also, in one embodiment, the display 28 includes a touch panel, such that the buttons, the tabs, the items or the like described above are manipulated, specified and selected and so forth by hands without the use of the mouse 31. Such use of the touch panel and the registration screen is also considered as the registration section, and a combination of the touch panel and the registration button 32c is also considered as the specifier for associating each of the target chart selection buttons 11a displayed in the list screen field 11A of the registration screen 33 with the target chart selection button screen field 11B.

Accordingly, it is possible to achieve the following (1) to (10) from the above-described exemplary embodiment of the present invention.

(1) A subjective optometric apparatus, including: a target-presenting device configured to display target charts for examining visual performance of eyes to be examined; an optical element-arranging device configured to set optical elements for optically correcting the visual performance of the eyes to be examined between the target-presenting device and the eyes to be examined; and a controller configured to control the target-presenting device and the optical element-arranging device, the controller including: a memory configured to store at least detailed contents of examinations to be performed on the eyes to be examined and the target charts; a display configured to display an operation screen including at least a target chart field corresponding to one of the target charts currently displayed on the target-presenting device and a target chart selection button screen field, the target chart selection button screen field having a plurality of changeover screen fields in which target chart selection buttons for selecting the corresponding target charts to be presented according to the examinations to be performed are arranged and displayed; a registration section configured to associate the detailed contents of the examinations and the target chart selection buttons and configured to register the associated target chart selection buttons; and a control section configured to control the target-presenting device to display one of the target charts selected by specification of a corresponding one of the target chart selection buttons of the target chart selection button screen field, and configured to control the optical element-arranging device such that one of the optical elements corresponding to the detailed contents associated with the specified one of the target chart selection buttons is set between the eyes to be examined and the target-presenting device.

(2) The subjective optometric apparatus according to (1), wherein the registration section includes a registration button and a specifier, the registration button is configured to changeover, from the operation screen, a registration screen including the target chart selection button screen field, the detailed contents associated with each of the target chart selection buttons, and a list screen field displaying a list of the target chart selection buttons, and configured to display the registration screen, and the specifier is configured to specify one of the target chart selection buttons displayed in the list screen field and configured to associate the specified one of the target chart selection buttons with one of the plurality of changeover screen fields.

(3) The subjective optometric apparatus according to (2), wherein the registration screen includes a modify button configured to changeover, from the registration screen, a modification setting screen for changing the detailed contents associated with one of the target chart selection buttons and setting the changed detailed contents in association with the one of the target chart selection buttons, and configured to display the modification setting screen, and the modification setting screen is configured to display the detailed contents associated with the one of the target chart selection buttons and includes a determine button configured to determine the association between the changed detailed contents and the one of the target chart selection buttons.

(4) The subjective optometric apparatus according to (3), wherein the display is configured to display, in the same one of the plurality of changeover screen fields of the target chart selection button screen field, the target chart selection buttons which are at least mutually identical and each associated with the detailed contents which are mutually different.

According to the above (1) to (4), the target chart selection button screen field including the plurality of changeover screens fields is provided so as to be changeable on the operation screen of the display, and the target chart selection button displayed and aligned in the changeover screen fields is selected to present the corresponding target chart. Therefore, it is possible for the examiner to promptly select the target chart to be displayed on the target-presenting device even when the number of target charts to be displayed on the target-presenting device is increased. Hence, it is possible to enhance the convenience of operation by the examiner and the convenience of examination of the eyes to be examined.

in addition, when the examination of the eyes is carried out on the program basis, it is possible to visually follow the flow of the entire examinations from the order of arrangement of the target chart selection buttons.

Furthermore, it is possible to perform an examination which is not incorporated in the program while the examination according to that program is carried out in a certain changeover screen field, by changing over the changeover screen fields of the target chart selection button screen field from the certain changeover screen field to another changeover screen field, and specifying the target chart selection button arranged and displayed in that other changeover screen field, at the discretion of the examiner. Thereby, it is possible for the examiner to perform the examination associated with the specified target chart selection button while the examination according to the program is carried out. Therefore, it is possible to perform a suitable examination in response to the examinee, flexibly.

In particular, according to the above (3), it is possible for the examiner to select the target charts to be used in the examination on the registration screen and to associate the detailed contents of the examination performed by using the selected target charts therewith. Therefore, it is possible to freely create an operation screen which is easy for the examiner to use.

(5) The subjective optometric apparatus according to (3), wherein the display is configured to display, in the different changeover screen fields of the plurality of changeover screen fields of the target chart selection button screen field, the target chart selection buttons which are at least mutually identical and each associated with the detailed contents which are mutually different.

According to the above (4) and (5), it is possible to set the detailed contents of the examinations which are different mutually to the identical target chart selection buttons, respectively. Therefore, it is possible to perform the plurality of examinations easily by using the identical target charts.

(6) The subjective optometric apparatus according to (3), wherein an order of the target chart selection buttons in the target chart selection button screen field of the operation screen is configured to be changeable by the specifier.

According to the above (6), it is possible to modify the order of the target chart selection buttons, easily. Therefore, alteration of an order of examinations becomes easy.

(7) The subjective optometric apparatus according to (1), wherein the target chart selection button screen field includes changeover buttons each configured to display the corresponding one of the plurality of changeover screen fields and each attached with information providing meaning to the corresponding one of the plurality of changeover screen fields.

(8) The subjective optometric apparatus according to (7), wherein the registration screen includes a setting button configured to changeover, from the registration screen, a meaning information modification screen for changing and setting the information attached to one of the changeover buttons, and configured to display the meaning information modification screen.

According to the above (7) and (8), since the meaning is given for each of the changeover screen fields, it is possible for the examiner to easily understand which one of the changeover screen fields contains the target chart selection buttons which correspond to the examinations the examiner desires to be performed.

(9) The subjective optometric apparatus according to (2), wherein the specifier includes a mouse device, and wherein the specified one of the target chart selection buttons is associated with the one of the plurality of changeover screen fields by moving the specified one of the target chart selection buttons to the one of the plurality of changeover screen fields by a drag-and-drop operation of the mouse device.

(10) The subjective optometric apparatus according to (8), wherein the specifier includes a mouse device, wherein the meaning information modification screen includes the target chart selection button screen field and a list screen configured to display a list having at least one of icons and characters, and wherein the information attached to the one of the changeover buttons of the target chart selection button screen field is changed by specifying one of the icons and the characters included in the list of the list screen of the meaning information modification screen and moving the specified one of the icons and the characters to the one of the changeover buttons by a drag-and-drop operation of the mouse device.

According to the above (9) and (10), it is possible to further enhance the convenience of operation by the examiner and the convenience of examination of the eyes to be examined.

Although the present invention has been described in terms of exemplary embodiments, it is not limited thereto. It should be appreciated that variations may be made in the embodiments described by persons skilled in the art without departing from the scope of the present invention as defined by the following claims. The limitations in the claims are to be interpreted broadly based the language employed in the claims and not limited to examples described in the present specification or during the prosecution of the application, and the examples are to be construed as non-exclusive. For example, in the present disclosure, the term "preferably", "preferred" or the like is non-exclusive and means "preferably", but not limited to. Moreover, no element or component in the present disclosure is intended to be dedicated to the public regardless of whether the element or component is explicitly recited in the following claims.

What is claimed is:
1. A subjective optometric apparatus, comprising:
a target-presenting device configured to display target charts for examining visual performance of eyes to be examined;
an optical element-arranging device configured to set optical elements for optically correcting the visual performance of the eyes to be examined between the target-presenting device and the eyes to be examined; and
a controller configured to control the target-presenting device and the optical element-arranging device,
the controller including:
a memory configured to store at least detailed contents of examinations to be performed on the eyes to be examined and the target charts;
a display configured to display an operation screen including at least a target chart field corresponding to one of the target charts currently displayed on the target-presenting device and a target chart selection button screen field, the target chart selection button screen field having a plurality of changeover screen fields in which target chart selection buttons for selecting the corresponding target charts to be presented according to the examinations to be performed are arranged and displayed;
a registration section configured to associate the detailed contents of the examinations and the target chart selection buttons and configured to register the associated target chart selection buttons; and
a control section configured to control the target-presenting device to display one of the target charts selected by specification of a corresponding one of the target chart selection buttons of the target chart selection button screen field, and configured to control the optical element-arranging device such that one of the optical elements corresponding to the detailed contents associated with the specified one of the target chart selection buttons is set between the eyes to be examined and the target-presenting device.

2. The subjective optometric apparatus according to claim 1, wherein the registration section includes a registration button and a specifier, the registration button is configured to changeover, from the operation screen, a registration screen including the target chart selection button screen field, the detailed contents associated with each of the target chart selection buttons, and a list screen field displaying a list of the target chart selection buttons, and configured to display the registration screen, and the specifier is configured to specify one of the target chart selection buttons displayed in the list screen field and configured to associate the specified one of the target chart selection buttons with one of the plurality of changeover screen fields.

3. The subjective optometric apparatus according to claim 2, wherein the registration screen includes a modify button configured to changeover, from the registration screen, a modification setting screen for changing the detailed contents associated with one of the target chart selection buttons and setting the changed detailed contents in association with the one of the target chart selection buttons, and configured to display the modification setting screen, and the modification setting screen is configured to display the detailed contents associated with the one of the target chart selection buttons and includes a determine button configured to determine the association between the changed detailed contents and the one of the target chart selection buttons.

4. The subjective optometric apparatus according to claim 3, wherein the display is configured to display, in the same one of the plurality of changeover screen fields of the target chart selection button screen field, the target chart selection buttons which are at least mutually identical and each associated with the detailed contents which are mutually different.

5. The subjective optometric apparatus according to claim 3, wherein the display is configured to display, in the different changeover screen fields of the plurality of changeover screen fields of the target chart selection button screen field, the target chart selection buttons which are at least mutually identical and each associated with the detailed contents which are mutually different.

6. The subjective optometric apparatus according to claim 3, wherein an order of the target chart selection buttons in the target chart selection button screen field of the operation screen is configured to be changeable by the specifier.

7. The subjective optometric apparatus according to claim 2, wherein the specifier includes a mouse device, and wherein the specified one of the target chart selection buttons is associated with the one of the plurality of changeover screen fields by moving the specified one of the target chart selection buttons to the one of the plurality of changeover screen fields by a drag-and-drop operation of the mouse device.

8. The subjective optometric apparatus according to claim 1, wherein the target chart selection button screen field includes changeover buttons each configured to display the corresponding one of the plurality of changeover screen fields and each attached with information providing meaning to the corresponding one of the plurality of changeover screen fields.

9. The subjective optometric apparatus according to claim 8, wherein the registration screen includes a setting button configured to changeover, from the registration screen, a meaning information modification screen for changing and setting the information attached to one of the changeover buttons, and configured to display the meaning information modification screen.

10. The subjective optometric apparatus according to claim 9, wherein the specifier includes a mouse device, wherein the meaning information modification screen includes the target chart selection button screen field and a list screen configured to display a list having at least one of icons and characters, and wherein the information attached to the one of the changeover buttons of the target chart selection button screen field is changed by specifying one of the icons and the characters included in the list of the list screen of the meaning information modification screen and moving the specified one of the icons and the characters to the one of the changeover buttons by a drag-and-drop operation of the mouse device.

* * * * *